United States Patent [19]

Buchanan

[11] Patent Number: 5,507,783
[45] Date of Patent: Apr. 16, 1996

[54] PACEMAKER MEDIATED TACHYCARDIA RESPONSE FOR VDD AND VDDR MODALITIES

[75] Inventor: Stuart W. Buchanan, Saugus, Calif.

[73] Assignee: Pacesetter, Inc., Sylmar, Calif.

[21] Appl. No.: 372,273

[22] Filed: Jan. 11, 1995

[51] Int. Cl.⁶ ...................................................... A61N 1/36
[52] U.S. Cl. ............................................. 607/14; 128/705
[58] Field of Search ....................... 607/14, 15; 128/697, 128/705

[56] References Cited

U.S. PATENT DOCUMENTS

| | | |
|---|---|---|
| 4,485,818 | 12/1984 | Leckrone et al. . |
| 4,539,991 | 9/1985 | Boute et al. . |
| 4,552,154 | 11/1985 | Hartlaub . |
| 4,554,920 | 11/1985 | Baker et al. . |
| 4,554,921 | 11/1985 | Boute et al. . |
| 4,569,350 | 2/1986 | Mumford et al. . |
| 4,624,260 | 11/1986 | Baker et al. . |
| 4,625,730 | 12/1986 | Fountain et al. . |
| 4,686,989 | 8/1987 | Smyth et al. ............................ 607/14 |
| 4,712,555 | 12/1987 | Thornander et al. . |
| 4,712,556 | 12/1987 | Baker . |
| 4,788,980 | 12/1988 | Mann et al. ............................ 607/14 |
| 4,809,697 | 3/1989 | Causey, III et al. . |
| 4,815,469 | 3/1989 | Cohen et al. . |
| 4,847,617 | 7/1989 | Silvian . |
| 4,856,523 | 8/1989 | Sholder et al. . |
| 4,860,749 | 8/1989 | Lehmann . |
| 4,940,052 | 7/1990 | Mann et al. . |
| 4,944,298 | 7/1990 | Sholder . |
| 5,074,308 | 12/1991 | Sholder et al. . |
| 5,085,215 | 2/1992 | Nappholz et al. . |
| 5,097,832 | 3/1992 | Buchanan . |
| 5,103,822 | 4/1992 | Duncan . |
| 5,144,949 | 9/1992 | Olson . |
| 5,156,147 | 10/1992 | Warren et al. . |
| 5,188,105 | 2/1993 | Keimel . |
| 5,205,283 | 4/1993 | Olson . |
| 5,228,438 | 7/1993 | Buchanan . |
| 5,312,450 | 5/1994 | Markwitz ............................... 607/14 |

Primary Examiner—William E. Kamm
Assistant Examiner—Jeffrey R. Jastrzab
Attorney, Agent, or Firm—Malcolm J. Romano

[57] ABSTRACT

A pacemaker mediated tachycardia (PMT) is detected and suppressed in an implantable pacemaker operating in the VDD or VDDR modality. Such suppression is effectuated by extending the post ventricular atrial refractory period (PVARP) of the pacemaker to an extended PVARP that prevents retrograde P-waves from being tracked, thereby suppressing the PMT. The extended PVARP includes a retrograde window portion, following an absolute refractory portion. P-waves that occur during the retrograde window portion of the extended PVARP are deemed to be retrograde P-waves. The extended PVARP is returned to its original value whenever: (1) a P-wave is sensed following the extended PVARP, which P-wave is deemed to be a sinus P-wave, or (2) whenever a sufficient number of cardiac cycles elapse without the occurrence of a retrograde P-wave.

24 Claims, 8 Drawing Sheets

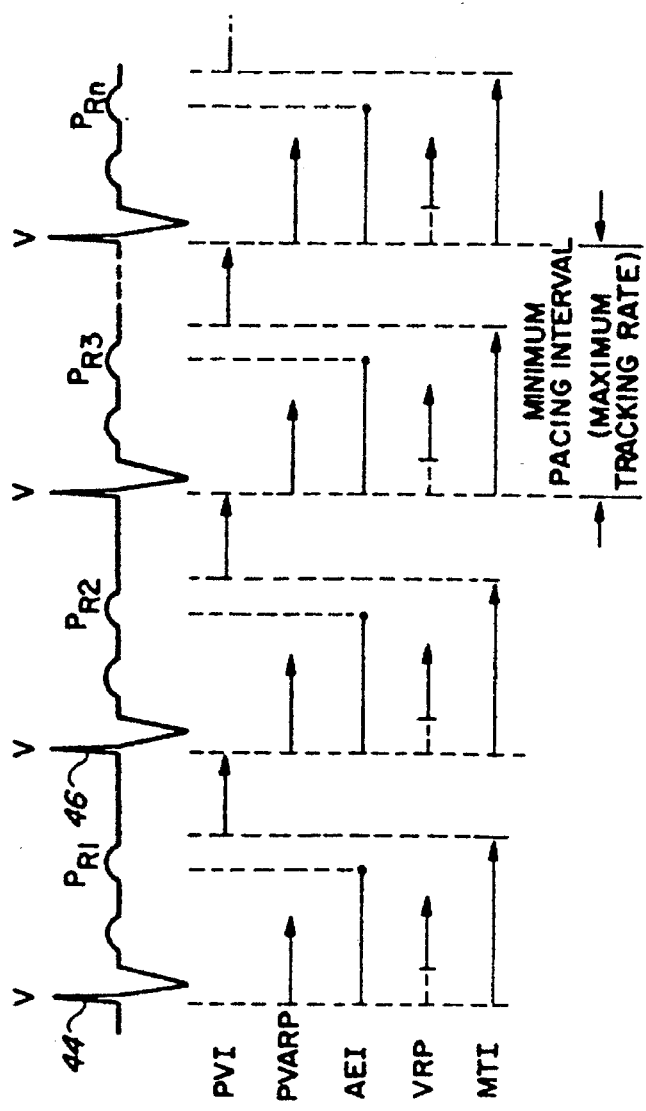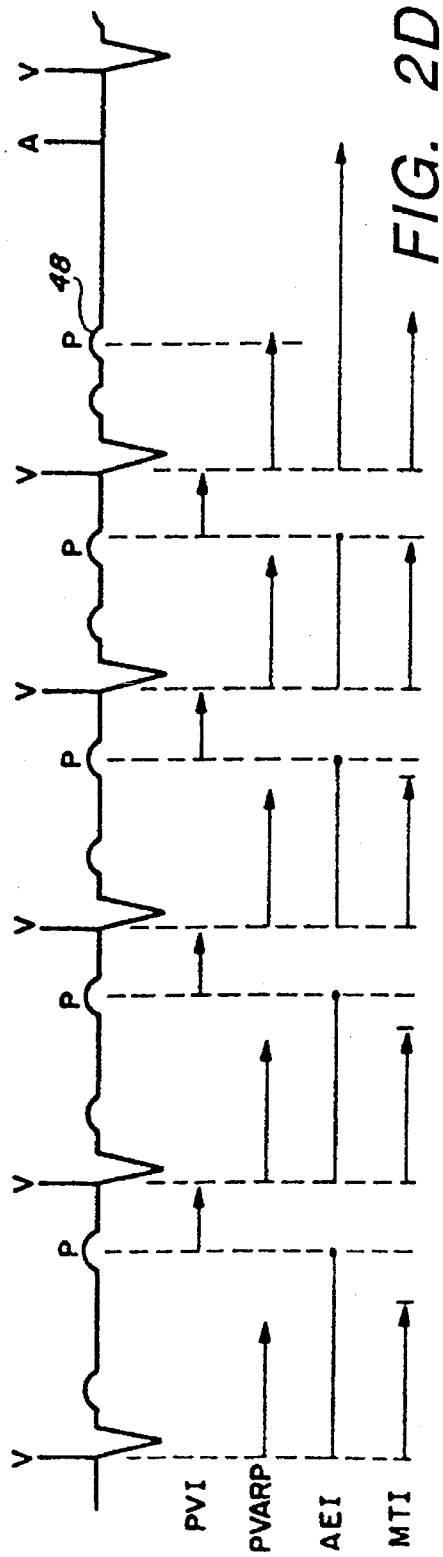

5,507,783

PACEMAKER MEDIATED TACHYCARDIA RESPONSE FOR VDD AND VDDR MODALITIES

BACKGROUND OF THE INVENTION

The present invention relates to cardiac pacemakers, and more particularly to implantable programmable cardiac pacemakers adapted to automatically detect and respond to the occurrence of a pacemaker-mediated tachycardia (PMT). Specifically, a pacemaker incorporating the present invention minimizes the likelihood that a PMT will be sustained; and further assures that when a true PMT is detected, an appropriate PMT response is invoked, in order to protect the pacemaker patient from remaining in a prolonged PMT condition which can not be terminated without atrial pacing.

In order to efficiently perform its function of a pump, the heart must maintain a natural AV synchrony. The term "AV synchrony" relates to the sequential timing relationship that exists between the contractions of the atria and the ventricles. In a given heart cycle or beat, the atria (A) contract prior to the ventricles (V) in accordance with a prescribed timing or synchronized relationship, hence the term "AV synchrony." These contractions are typically manifest or measured by sensing electrical signals or waves that are attendant with the depolarization of heart tissue, which depolarization immediately precedes (and for most purposes can be considered concurrent with) the mechanical contraction of the cardiac tissue. These signals or waves can be viewed on an electrocardiogram (ECG) and include a P-wave, representing the depolarization of the atria; the QRS-wave (sometimes referred to as an R-wave, the predominant wave of the group), representing the depolarization of the ventricles; and the T-wave, representing the repolarization of the ventricles. (It is noted that the atria also are repolarized, but this atrial repolarization occurs at approximately the same time as the depolarization of the ventricles; and any electrical signal generated by atrial repolarization is generally minute and masked out by the much larger QRS-wave on the ECG.)

A pacemaker is a medical device that assists the heart in maintaining a desired AV synchrony by monitoring the atria and/or ventricles for the occurrence of P-waves and/or R-waves, and by producing stimulation pulses that are delivered to an appropriate chamber of the heart to cause that chamber to depolarize, and hence contract. (Because the main function of the pacemaker is to provide such stimulation pulses, a pacemaker is frequently referred to as a "pulse generator.") If for some reason the heart is unable to maintain its natural AV synchrony, a pacemaker is utilized to monitor the heart and to provide electrical stimulation pulses when it senses the heart is not maintaining a proper AV synchrony. A VDD or VDDR-type pacemaker, for example, monitors both the right atrium and right ventricle. If it senses an atrial depolarization and ventricular depolarization within a prescribed time after the atrial depolarization, no ventricular stimulation pulse is generated. If however, it fails to sense either the atrial or ventricular depolarization within prescribed time periods, then ventricular stimulation pulses, frequently referred to as V-pulses, are generated and delivered to the ventricular chamber of the heart at an appropriate time in order to maintain the correct heart rhythm.

One of the problems that complicates the operation of a VDD or VDDR-type pacemaker, i.e., one that is capable of sensing in both chambers of the heart and pacing in the ventricular chamber, is "retrograde conduction." Retrograde conduction occurs when the depolarization of the ventricles propagates backwards into the atria, causing the atria to depolarize prematurely. This atrial depolarization is manifest by the occurrence of a P-wave, frequently referred to as a "retrograde P-wave." A retrograde P-wave appears on the ECG to be substantially the same as a natural P-wave except that it occurs much too soon after a ventricular contraction. The retrograde P-wave follows the ventricular contraction by a relatively constant period of time that is a function of the electrical conduction path through which the depolarization of the ventricles propagates backwards. (A "natural" P-wave results from the natural AV synchrony of the heart as set by the heart's natural sinus rhythm, and is hereafter referred to as a "sinus" P-wave.) See U.S. Pat. No. 4,788,980, incorporated herein by reference, for a more thorough description of retrograde conduction.

Unfortunately, many VDD and VDDR-type pacemaker sensing circuits cannot readily distinguish between a retrograde P-wave and a sinus P-wave. A significant problem thus arises because once a P-wave is sensed, the VDD or VDDR pacemaker will typically generate a V-pulse a prescribed delay thereafter, referred to herein as the "P-V delay," unless an R-wave is sensed during the P-V delay. (It is noted that much of the literature refers to the P-V delay, as that term is used herein, as the "AV delay," or AVD. Further, some pacemakers employ one delay, a P-V delay, following a P-wave, and another slightly different delay, or AV delay, following an A-pulse. For purposes of the present invention, all such delays following an atrial event, whether an A-pulse or P-wave, are referred to herein as the "P-V delay.") If the sensed P-wave is a retrograde P-wave, an R-wave will not likely occur during this relatively short P-V delay time interval because the contraction of the ventricles just occurred prior to the retrograde P-wave. Thus, at the conclusion of the P-V delay, a V-pulse is generated by the pacemaker, causing the ventricles to again contract, which contraction causes another retrograde P-wave. This retrograde P-wave, in turn, causes another V-pulse to be generated after the P-V delay, causing the cycle to repeat, resulting in a pacemaker mediated tachycardia, or PMT. (A "tachycardia" is a very rapid rhythm or rate of the heart.)

Note that during a PMT, it is the pacemaker itself that causes or "mediates" the tachycardia by tracking each P-wave caused by retrograde conduction, and providing a ventricular stimulation pulse a programmed P-V delay thereafter. The pacemaker thus provides the forward conduction path (from the atria to the ventricles) electronically by tracking each P-wave and generating a V-pulse (ventricular stimulation pulse) if no R-wave is sensed within a prescribed time thereafter (the programmed P-V delay). The reverse or backward conduction path (from the ventricles to the atria) is provided by retrograde conduction originating with the depolarization of the ventricles, which depolarization occurs as a result of the V-pulse. Thus, retrograde conduction passes the ventricular depolarization back to the atria, causing the atria to depolarize (resulting in a retrograde P-wave), and the process repeats.

Unfortunately, a PMT can be triggered by numerous events. The most common mechanism for triggering a PMT is a premature ventricular contraction, or PVC. A PVC, in turn, is not an uncommon occurrence for most mammalian hearts. A cough or a sneeze, for example, may cause a PVC. Unfortunately, for a patient having a VDD or VDDR-type pacemaker, the occurrence of a single PVC can reset the pacemaker timing in a manner that allows the pacemaker to begin tracking retrograde P-waves, causing a PMT to occur. Such PMT, if allowed to continue for more than just a few cycles, seriously impacts the ability of the heart to efficiently perform its function of a pump. What is needed, therefore, is a system or method for accurately detecting the occurrence of a true PMT, i.e., a tachycardia that is in fact mediated by the pacemaker, and quickly respond to such true PMT once detected.

In the VDDR modality, sensor drive of the ventricular rate can also initiate retrograde conduction at various sensor rates, thereby causing a PMT if the retrograde P-wave occurs outside of the post ventricular atrial refractory period (PVARP) interval. Since the VDDR mode only senses in the atrial chamber, the absence of atrial pacing will only encourage retrograde conduction and PMT's. There is, therefore, a need to protect the pacemaker patient from endlessly tracking retrograde P-waves, which may result in high ventricular maximum tracking rates and loss of AV synchrony. In addition, traditional PMT breaking algorithms may not be able to break a PMT in the VDDR modality, since there is no atrial pacing to break the cycle of retrograde conduction. This invention addresses a new PMT response (i.e., suppression) which will protect the pacemaker patient from remaining in a prolonged PMT condition which can not otherwise be terminated due to the absence of atrial pacing and a method to allow sinus P-wave tracking if sinus activity is present.

SUMMARY OF THE INVENTION

The present invention advantageously addresses the needs above as well as other needs by providing a pacemaker, and a method for operating the same, that minimizes the likelihood that a PMT will be sustained; and that further assures that when a true PMT is detected, an appropriate PMT response is invoked for only as long as is needed.

The invention may be characterized as a method for detecting and responding to a true PMT, including the steps of: (a) detecting a true PMT; (b) issuing a PMT response; and (c) discontinuing the PMT response when no longer needed. The PMT is detected using conventional methods. The PMT response comprises increasing a PVARP (post ventricular atrial refractory period) of the pacemaker to an extended PVARP. The PMT response is automatically stopped or discontinued whenever either: (1) a sinus P-wave occurs after the extended PVARP, or (2) retrograde P-waves are no longer detected during a retrograde conduction time window located within the latter portion of the extended PVARP. As will be discussed later in detail, it should be noted that the term PMT response is used in a broad sense and is intended to include PMT suppression.

The invention may further be characterized as an implantable pacemaker that carries out the above method. Such pacemaker includes detecting means for detecting a PMT and PMT response means for responding to the detected PMT. Advantageously, the PMT response means includes means for automatically discontinuing the PMT response when detected conditions indicate the PMT response is no longer needed.

The preferred means for detecting a PMT involves looking for a P-V-P-V-P-V . . . sequence that defines a cardiac rate greater than a prescribed tachycardia threshold rate, and checking the V-P interval of a prescribed number of pacing cycles within the sequence to see if the V-P interval changes when the P-V interval is changed. If a PMT is present, the V-P interval is largely based on the retrograde condition time, and will not change. In contrast, if a PMT is not present, then the V-P interval will change as required to make up for deliberate changes made to the P-V interval. This technique for detecting a PMT is substantially as described in applicant's prior patent U.S. Pat. No. 5,074,308.

The PMT response means invoked upon detecting a PMT includes means for extending the PVARP by either: (1) a programmed amount so that the total extended PVARP is between 200 ms and 550 ms; or (2) a calculated amount so that the total extended PVARP is equal to the longest V-P interval measured during a prescribed number of previous cardiac cycles plus a safety margin. Advantageously, by extending PVARP to the calculated amount based on the longest V-P intervals previously measured, any sinus P-waves that might occur have a better chance of being detected, and hence tracked, thereby providing for A-V synchrony. This is particularly important when the patient is exercising, or at other times of stress, so as to cause the sinus rate to increase. At such times of increased sinus rate, a programmed extension of the PVARP (as in option (1) above) might preclude sinus P-waves from being sensed at the faster rate.

The PMT response means also includes means for returning the extended PVARP to its original value whenever sinus P-waves occur or whenever retrograde P-waves fail to occur. More particularly, any P-waves that occur after the extended PVARP are deemed to be non-retrograde P-waves, i.e., sinus P-waves. The occurrence of such sinus P-waves provides an indication that the PMT response (the extended PVARP) may no longer be needed. Hence, if a prescribed number, e.g., 1 to 10, of such sinus or non-retrograde P-waves consecutively occur, then the extended PVARP is returned to its original value. Further, any P-waves that occur during a retrograde window portion of the extended PVARP (comprising the latter portion of the extended PVARP) are deemed retrograde P-waves. The consecutive nonoccurrence of a prescribed number of such retrograde P-waves is also an indication that the PMT response is no longer needed. Hence, when a programmed number n, where n is, e.g., 1 to 255, of retrograde windows occur without any retrograde P-waves having being sensed therein, and without any sinus P-waves having occurred outside of the retrograde window, then the extended PVARP reverts back to its initial value. Being able to program the number n of consecutive retrograde P-waves that must fail to occur before the PMT response is terminated advantageously allows for the occasional non-sensing of a retrograde P-wave, as might occur, e.g., due to a marginal atrial sense threshold, or due to the occurrence of a retrograde P-wave during an absolute refractory portion of PVARP.

The present invention is particularly suited for use with pacemakers operating in the VDD or VDDR modalities. This is because such modalities only sense in the atrial chamber, and are not capable of pacing in the atrial chamber. The absence of atrial pacing to begin the cardiac cycle disadvantageously increases the likelihood of retrograde conduction, and hence a PMT. However, by using the present invention within a VDD or VDDR pacer, such likelihood is significantly reduced because true PMT's are detected, and when detected are stopped by increasing PVARP so as to block the tracking of retrograde P-waves associated with the PMT. Further, the present invention also quickly returns PVARP back to its original value after the PMT has stopped, thereby allowing sinus P-waves to be tracked so that the proper A-V synchrony can be maintained.

It is therefore a feature of the invention to provide a pacemaker and method for operating the same that provides for the detection and suppression of pacemaker mediated tachycardia (PMT).

It is another feature of the invention to provide for such detection and suppression in a pacemaker operating in a VDD or VDDR modality.

It is an additional feature of the invention to provide for such detection and suppression in an environment that affords sinus P-waves every opportunity to be sensed and tracked, and to thus provide A-V synchrony, especially when the patient is exercising or at other times when the sinus rate increases.

It is a further feature of the invention to suppress PMT's by extending a PVARP interval by either a programmed amount or by an amount dependent on a V-P interval plus a safety margin. It should also be noted that suppression as used herein means that retrograde P-waves are no longer tracked due to PVARP extension. As a result, retrograde P-waves may however still occur during cardiac cycles; however, they will be "masked" and therefore will not be considered as sinus P-waves to effect (i.e., normally to increase) the pacing rate.

It is also a feature of the invention to restore PVARP to its original length upon the occurrence of a sinus P-wave, where a sinus P-wave is deemed to be any P-wave that occurs after the extended PVARP.

It is an additional feature of the invention to also restore the PVARP to its original length upon the non-occurrence of a programmed number of retrograde P-waves. More particularly, it is a feature of the invention to deem all atrial activity (P-waves) sensed within a retrograde window portion of the extended PVARP as a retrograde P-wave. Thus, when a programmed number n of such P-waves fail to occur, that serves as an indication that the retrograde P-waves have stopped, so PVARP is returned to its initial value.

BRIEF DESCRIPTION OF THE DRAWINGS

The above and other aspects, features and advantages of the present invention will be more apparent from the following more particular description thereof, presented in conjunction with the following drawings wherein:

FIG. 2C is a composite timing diagram illustrating a PMT at the maximum tracking rate (MTR) of the pacemaker;

FIG. 2D is a composite timing diagram illustrating a sinus rate greater than the MTR of the pacemaker;

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
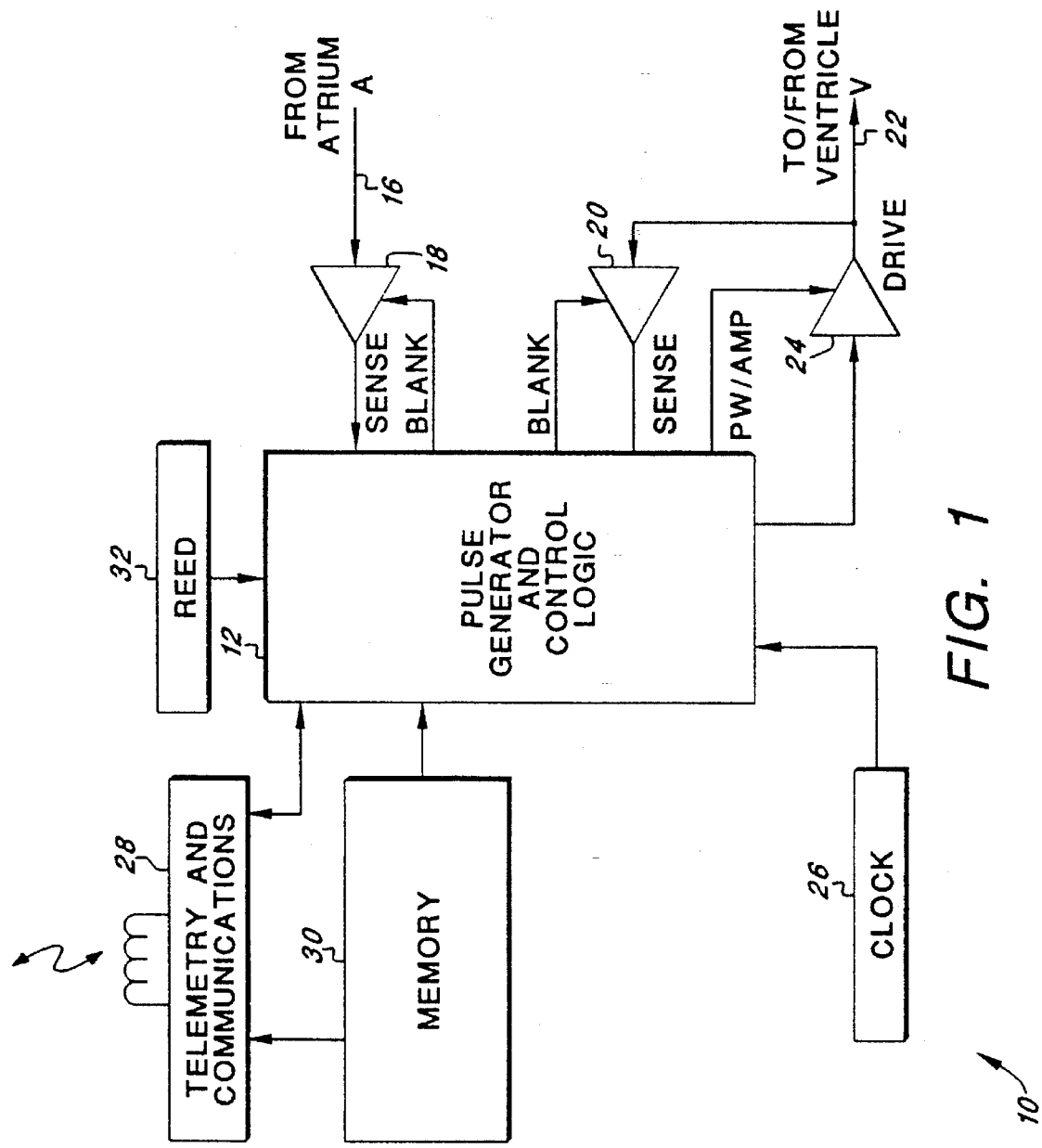
FIG. 1 is a block diagram of an implantable, programmable, VDD or VDDR-type pacemaker.

Referring to FIG. 1, a functional block diagram of a typical VDD or VDDR-type pacemaker 10 is illustrated. The circuitry shown may be used to carry out the PMT recognition and suppression method of the present invention. Pulse Generator and Control Logic 12 generates the appropriate timing signals and sequences to enable stimulation pulses to be generated and delivered to the heart. An atrial lead 16 is connected to an atrial sense amplifier 18 that monitors electrical activity of the right atrium to determine if a sinus P-wave, representing the natural depolarization of the atrium, has occurred. If such sinus atrial activity is sensed, then Pulse Generator and Control Logic 12 provides for a ventricular stimulus after a predetermined time period (referred to as the P-V delay).

In a similar manner, the Pulse Generator and Control Logic 12 senses the electrical activity occurring in the right ventricle of the heart through a sense amplifier 20 connected to a ventricular lead 22. If naturally occurring ventricular electrical activity is not sensed within an appropriate escape interval, then the Pulse Generator and Control Logic 12 generates a ventricular stimulation pulse ("V-pulse") of a prescribed pulse width and amplitude, delivered through the drive amplifier 24, in order to cause the desired ventricular contraction. If naturally occurring ventricular electrical activity is sensed, i.e., if an R-wave is sensed, then the Pulse Generator and Control Logic 12 inhibits the pulse provided to the drive amplifier 24 and resets the pacemaker timing logic within the Pulse Generator and Control Logic 12. Suitable leads for use with the present invention are described in U.S. Pat. No. 4,815,469, incorporated herein by reference.

Clock circuitry 26 provides the basic clock signals or timing signals from which the Pulse Generator and Control Logic 12 operates. Telemetry and communications circuitry 28 provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulating pulse, as well as other control parameters used within the pacemaker. Such control information may also be passed directly to the Pulse Generator and Control Logic 12, if desired. Similarly, electrical activity of the heart, as sensed through the sense amplifiers 18 and 20, can be telemetered external to the pacemaker through the telemetry and communications circuitry 28, thereby allowing an attending physician or other medical personnel, e.g., cardiologist, to monitor the activity of the heart without the use of external skin electrodes.

A magnetic reed switch 32 is also typically employed with implanted pacemakers in order to control the programmable functions of the device. With a suitable programming apparatus in place, the reed switch 32 is closed and the attending physician or cardiologist can effectuate any desired changes in the operation of the pacemaker by sending appropriate control signals and commands over the telemetry and communications circuitry 28. Without the appropriate programming apparatus, the reed switch 32 remains open, and the telemetry and communications circuitry 28 is not operable. An external programmer suitable for use with the present invention is described in U.S. Pat. No. 4,809,697, incorporated herein by reference.

Note that the above-described VDD or VDDR-type pacemaker, or any other type of pacemaker suitable for use with the present invention, can also be implemented using a microprocessor-based design. One example of such a design is shown in U.S. Pat. No. 4,940,052, incorporated herein by reference. Other possible implementations are shown, for example, in U.S. Pat. No. 4,712,555, wherein a state-machine-type implementation is described; and U.S. Pat. No. 4,944,298, wherein an atrial-rate-based programmable pacemaker is described; both of which are incorporated herein by reference.

Figure 2A:
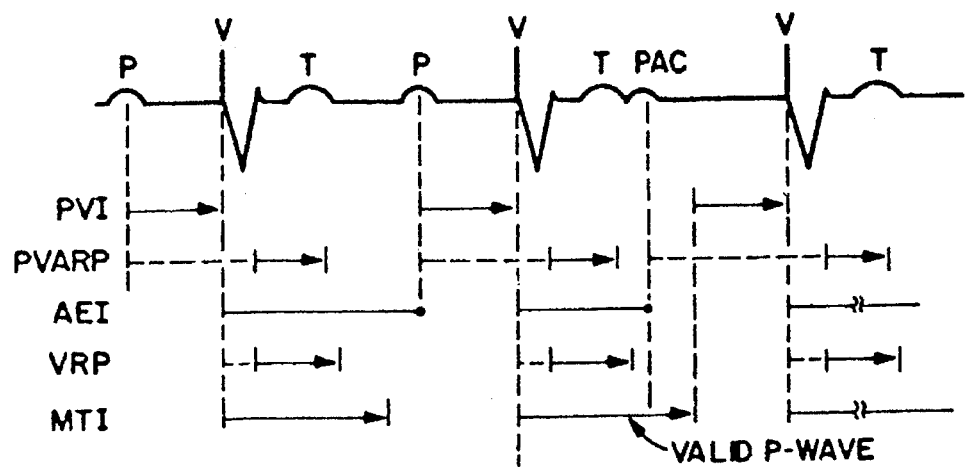
FIG. 2A is a composite timing diagram illustrating how AV synchrony is maintained when ventricular stimulation pulses are provided to the heart, and further illustrates one possible response of a pacemaker to a premature atrial contraction (PAC)

Referring next to FIG. 2A, a composite timing diagram is shown of illustrating how AV synchrony is maintained when ventricular stimulation pulses are provided to the heart. In this and other timing diagrams used herein, the stimulation pulses generated by the pacemaker are illustrated as a narrow spike labeled with a V (for a ventricular stimulation pulse).

The time intervals shown in the timing diagrams that follow are indicated by a horizontal line. If the time interval has "timed-out"—that is, if it has reached its terminal count—an arrowhead is placed on the horizontal line, pointing to the point in time at which the time interval terminates. (The horizontal axis of the timing diagrams represents the time axis.) It is noted that the timing drawings are not necessarily drawn to scale, nor with linear horizontal or vertical axes. It is also noted that some cardiac events, such as the T-wave, may be omitted from some of the timing diagrams. If a sensed electrical event occurs prior to the termination of a given interval, which event inhibits the generation of a stimulation pulse (or alters some other operation of the pacemaker) then a dot is placed on the horizontal line indicating the point in time at which the sensed event terminates or resets that particular interval.

Shown are five basic time intervals. These five time intervals are not the only time intervals defined by the Control Logic 12 and used in the operation of a pacemaker, but are some of the most pertinent time intervals utilized by the present invention. These five intervals are: (1) the P-V interval, or PVI, representing the desired time interval between atrial depolarization and ventricular depolarization; (2) the post ventricular atrial refractory period, or PVARP, representing the time interval subsequent to a ventricular event during which the atrial sensing circuits are disabled; (3) the atrial escape interval, or AEI, representing the time interval between an R-wave or V-pulse and a subsequent P-wave (sometimes also referred to as the V-P interval or the VA interval); (4) the ventricular refractory period, or VRP, representing the interval during which the ventricular sense amplifier 20 (FIG. 1) is disabled; and (5) the maximum tracking interval, or MTI, representing the interval that defines the maximum tracking rate at which the pacemaker may operate. (The intervals MTI+PVI thus define the shortest possible time period of a pacemaker-defined cardiac cycle, and hence, the maximum possible paced ventricular rate.)

As shown in FIG. 2A, when the sinus P-wave is sensed, the P-V interval, PVI, is initiated, and the pacemaker is alert in order to sense if an R-wave will occur. If an R-wave has not been sensed by the time the P-V interval times-out, then a V-pulse is generated as indicated. This V-pulse initiates the beginning of the atrial escape interval and PVARP. Prior to the termination of the AEI, a naturally-occurring P-wave is sensed, indicated by the dot on the AEI line. The sensing of the naturally-occurring P-wave initiates the beginning of a new P-V interval, at the conclusion of which another V-pulse is generated. This process continues for so long as the heart continues to generate sinus P-waves but fails to produce naturally-occurring R-waves.

FIG. 2A further illustrates one possible response of the pacemaker to a premature atrial contraction, or PAC. A premature atrial contraction is simply a contraction of the atrium that occurs prematurely or early in the normal AV synchrony. The PAC shown in FIG. 2A occurs immediately subsequent to the second T-wave. The pacemaker responds to the PAC as though it were a sinus P-wave. That is, the occurrence of the PAC terminates the atrial escape interval. Further, when a P-wave occurs within MTI, as does the PAC shown in FIG. 2A, a latch circuit is set indicating that the sensed activity is considered a valid P-wave. The setting of this latch causes the P-V interval to be initiated at the end of the MTI. At the conclusion of this A-V interval, the V-pulse is generated. Once a V-pulse has been generated, the operation of the pacemaker continues in normal fashion.

Figure 2B:
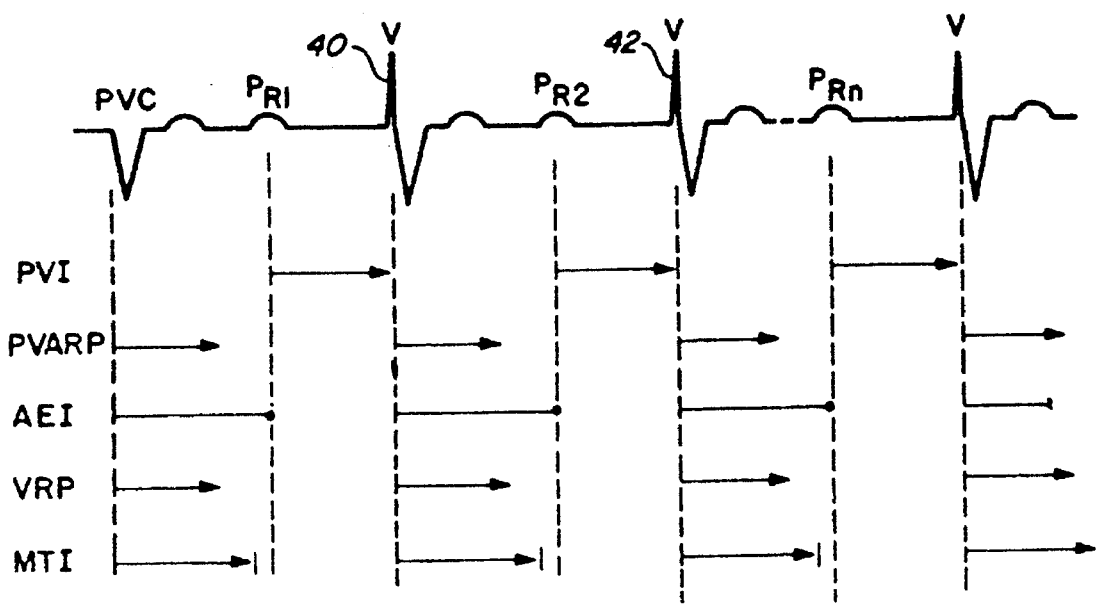
FIG. 2B is a composite timing diagram illustrating a PMT at a rate less than the maximum tracking rate (MTR) of the pacemaker.

Referring to FIG. 2B, a composite timing diagram as in FIG. 2A illustrates a PMT at a rate less than the maximum tracking rate (MTR) of the pacemaker. (The MTR of the pacemaker, as shown in FIG. 2C, is determined by the MTI plus the PVI.) A ventricular contraction, e.g., a PVC, triggers a first retrograde P-wave, $P_{R1}$, through retrograde conduction as previously described. This retrograde P-wave is interpreted by the pacemaker sensing circuits as a normal P-wave. Thus, its occurrence triggers a P-V interval, PVI. At the conclusion of the PVI, a V-pulse 40 is generated. This V-pulse 40 causes the ventricles to contract, which contraction causes a second retrograde P-wave, $P_{R2}$, to occur. The second retrograde P-wave again triggers a P-V interval, PVI, at the conclusion of which a second V-pulse 42 is generated. The ventricular contraction caused by this second V-pulse 42 causes another retrograde P-wave, and the process repeats.

Note, as seen in FIG. 2B, that the time interval between a ventricular contraction and the occurrence of a retrograde P-wave, PR, is longer than the minimum tracking interval, MTI. Hence, e.g., assuming the minimum tracking interval is 270 msec., and the PVI is 130 msec., the minimum pacing interval (MTI+PVI) is 400 msec.,corresponding to a maximum tracking rate (MTR) of approximately 150 bpm (beats per minute). However, because the P-V interval (controlled by the retrograde conduction time) is longer than the MTI, the overall pacing interval, and hence the PMT rate, is greater than 400 msec., resulting in a PMT rate less than the MTR. For example, if the P-V interval is on the order of 310 msec. (some 40 msec. longer than the MTI), then the overall pacing interval is 440 msec., corresponding to a PMT rate of about 136 bpm.

Referring next to FIG. 2C, a composite timing diagram illustrates a PMT condition wherein the PMT is constrained to operate at the maximum tracking rate (MTR). In FIG. 2C, it is assumed that this PMT condition is already established. Thus, a V-pulse 44 causes a first retrograde P-wave $P_{R1}$ to occur. This P-wave $P_{R1}$ occurs after the V-pulse 44 at a time that is subsequent to the termination of the PVARP (and hence at a time when the P-wave can be sensed), but is prior to the termination of the MTI. The programmed P-V interval, or PVI, cannot begin until the MTI times-out. In this regard, the retrograde P-wave $P_{R1}$ is similar to the PAC shown in FIG. 2A. After the termination of the minimum tracking interval MTI, the programmed P-V interval, PVI, begins, after which another V-pulse 46 is generated. A second retrograde P-wave $P_{R2}$ occurs prior to the termination of the next MTI, which MTI is triggered by the V-pulse 46. This process continues, with the retrograde P-wave always occurring prior to the termination of the MTI interval, the PVI not starting until the MTI times-out, and the V-pulse being generated at the conclusion of the pacemaker-defined PVI.

Referring next to FIG. 2D, a composite timing diagram illustrates an increasing sinus rate that ends up greater than the pacemaker-defined MTR. The sinus rate is initially sensed by the occurrence of P-waves that occur prior to the termination of the atrial escape interval, AEI, but after the termination of PVARP. The ventricle is stimulated with a V-pulse at the conclusion of the P-V interval (PVI), or programmed P-V delay, which interval or delay is triggered by the occurrence of a P-wave. The interval between the V-pulse and the subsequent P-wave, i.e., the V-P interval, gets progressively shorter until a P-wave 48 falls into PVARP. Once a P-wave falls into PVARP it is not sensed.

It is significant to note for purposes of the present invention that the V-P interval for a sinus rate is not stable. That is, it changes from cycle to cycle, as seen in FIG. 2D. In contrast, for the PMT conditions illustrated in FIGS. 2B and 2C, the V-P interval is more or less stable for each cycle. This is because for the situation where the P-wave is a retrograde P-wave, the entire V-P interval is essentially the retrograde conduction time, which conduction time is more or less constant for a given average cardiac rate. Thus, regardless of whether the PMT is at a rate less than the MTR or equal to the MTR, the V-P interval portion of each PMT cycle is more or less stable, even though other portions of the PMT cycle, e.g., the P-V portion, may momentarily change. This distinction, wherein a PMT includes a stable V-P interval and a non-PMT does not, provides the basis by which the system and method of the present invention is able to recognize whether a fast heart rate condition is a PMT or a non-PMT. Such recognition of PMT/non-PMT is explained fully in U.S. Pat. No. 5,074,308, incorporated herein by reference.

In accordance with the present invention, a system and method for recognizing and responding to a PMT is provided. Broadly stated, the recognizing-a-PMT portion of this system may be described as a system for detecting a pacemaker mediated tachycardia (PMT) in a patient having an implantable pacemaker. The detection system includes: (1) first detection means within the pacemaker for detecting a prescribed sequence of cardiac cycles, this prescribed sequence comprising a P-wave followed by a V-pulse at a rate faster than a reference rate, and wherein the time interval between the P-wave and the V-pulse of each cardiac cycle, or the P-to-V interval, comprises a "P-V delay"; (2) means responsive to the first detection means for momentarily changing the P-V delay in a selected cycle; and (3) second detection means for detecting if a V-P interval associated with the selected cardiac cycle remains substantially unchanged from a V-P interval associated with at least one cardiac cycle immediately preceding the selected cardiac cycle. The detection system is described more completely in U.S. Pat. No. 5,074,308, previously referenced.

The V-P interval comprises the time interval between a V-pulse and the occurrence of a P-wave. A substantially unchanged V-P interval associated with the cardiac cycle wherein the P-V delay has been changed (relative to a V-P interval of an adjacent cardiac cycle wherein the P-V delay has not been changed) provides an indication that the prescribed sequence of cardiac cycles comprises a PMT. On the other hand, a V-P interval that is substantially changed provides an indication that the prescribed sequence of cardiac cycles is not a PMT.

Advantageously, the conventional circuits within the VDD or VDDR-type pacemaker, e.g., as described above in connection with FIG. 1, or as otherwise known in the art, may be used to monitor the cardiac cycle and to determine if the cardiac cycle is of the prescribed type (i.e., a cardiac cycle wherein P-wave tracking occurs as manifest by a P-wave being sensed in each cycle followed by a V-pulse being generated after the programmed PV delay). These same conventional circuits may be used to determine if the rate of the cardiac cycle exceeds a reference rate.

Figure 3:
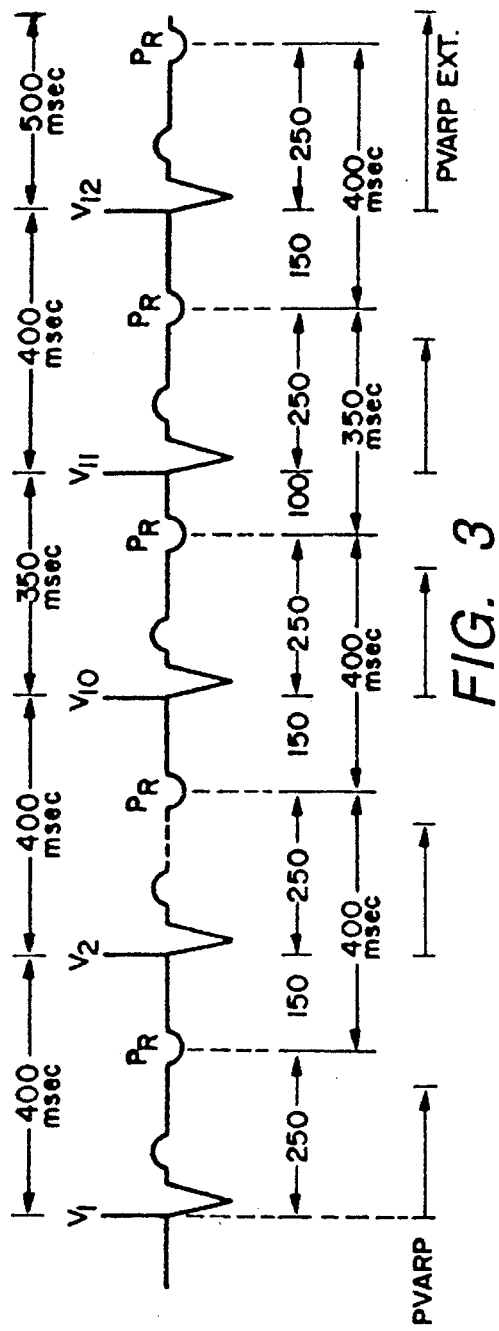
FIG. 3 is a composite timing diagram showing the detection of a PMT in accordance with one embodiment of the invention.

A PMT condition is illustrated in FIG. 3. A first V-pulse, $V_1$, and a second V-pulse, $V_2$, are separated by 400 msec., which time is less than the programmed minimum tracking interval. The cardiac cycle measured between $V_1$ and $V_2$ is comprised of a V-to-P interval of 250 milliseconds (msec), and a P-to-V interval of 150 msec. The P-to-V interval is set by the programmed PV delay of the pacemaker. Additional V-pulses, not shown, up to a tenth V-pulse, $V_{10}$, are similarly separated by approximately 400 msec.,making a total of nine (9) cardiac cycles (measured from V-pulse to V-pulse) that have occurred sequentially, each containing the requisite P-wave and V-pulse. During each cycle, the V-P interval is measured. The average V-P interval is then computed over the nine cardiac cycles to be 250 msec.

In accordance with one embodiment of the invention, after the prescribed number of cardiac cycles meeting the specified criteria have occurred, e.g., nine cardiac cycles, each having a V-to-V interval less than the reference interval, with each interval containing a P-wave followed by a V-pulse, the P-V delay of the next cardiac cycle is shortened by a prescribed amount, e.g., 50 msec. Thus, in FIG. 3, after the 10th V-pulse, $V_{10}$, the P-V delay of the next cardiac cycle is shortened by 50 msec. This causes the next P-V interval to be equal to 100 msec., which action also shortens the total V-V interval between $V_{10}$ and $V_{11}$ to 350 msec., because the V-P interval (which in this instance is essentially the retrograde conduction time) remains approximately the same. After shortening the P-V delay for one cycle, it is restored to its original value of 150 msec. Thus, during the next V-V interval, between $V_{11}$ and $V_{12}$, the P-V portion is restored to 150 msec., and the total V-V interval time returns to 400 msec. Because the V-P interval subsequent to shortening the P-V delay remains substantially unchanged from the V-P intervals prior to shortening the P-V delay, e.g., at 250 msec., a PMT is indicated. Thus, an appropriate PMT termination regimen, described below, is invoked.

Figure 4:
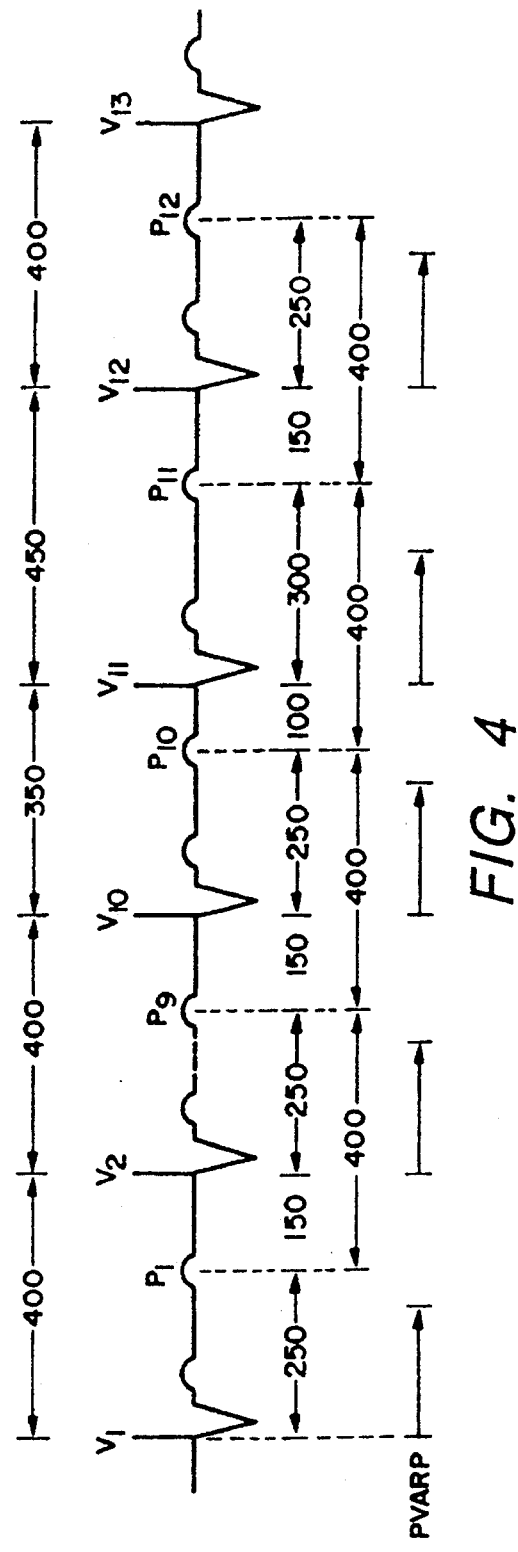
FIG. 4 is a composite timing diagram showing how the embodiment of FIG. 3 properly recognizes a sinus drive as a non-PMT condition.

Referring next to FIG. 4, a non-PMT condition is illustrated. As in FIG. 3, it is assumed that a prescribed number of cardiac cycles has occurred, each having a P-wave followed by a V-pulse, and each having a V-V interval less than the prescribed reference, or tachycardia reference rate (TRR). Hence, in accordance with this embodiment of the invention, the P-V delay is shortened by 50 msec. Thus, during the next V-V interval, between $V_{10}$ and $V_{11}$, the P-V delay is shortened to 100 msec. However, this action causes the next V-P interval, between $V_{11}$ and $P_{11}$, to also change. In this case, the amount of change is shown as an additional 50 msec., although this increase is only exemplary. In any event, because the V-P interval is not dominated by a retrograde conduction time, the V-P interval following the shortened P-V delay is substantially different than the average V-P interval measured during the previous cardiac cycles, e.g., from $V_1$ through $V_{10}$. Hence, the method illustrated operates to find the tachycardia condition represented in FIG. 4 as not being a PMT, but rather a sinus drive condition. Accordingly, a PMT termination regimen is not necessary nor desired.

In general, then, the above described method can further be characterized as a method for detecting a PMT that includes the steps of:

(a) sensing a P-wave followed by a V-pulse in a plurality of successive cardiac cycles;

(b) sensing if the plurality of successive cardiac cycles sensed in step (a) occurs at a rate in excess of a tachycardia reference rate (TRR);

(c) increasing or decreasing a P-V delay in a single cardiac cycle when the rate of the plurality of successive cardiac cycles sensed in step (b) exceeds the TRR;

(d) measuring a V-V time interval associated with the single cardiac cycle of step (c), this V-V time interval comprising the elapsed time between a first V-pulse and a second V-pulse, a first P-wave occurring after the first V-pulse and prior to the second V-pulse, and the increased P-V delay of step (c) being included in the V-V time interval as the time interval between the first P-wave and the second V-pulse;

(e) measuring a P-P time interval associated with the single cardiac cycle of step (c), this P-P time interval comprising the elapsed time between a first P-wave and a second P-wave, the second P-wave occurring after the second V-pulse, and the increased P-V delay of step (c) being included in the P-P time interval as the time interval between the first P-wave and the second V-pulse;

(f) measuring the difference between the V-V time interval and the P-P time interval; and (g) indicating a PMT condition when the difference between the V-V time interval and the P-P time interval is less than a prescribed difference.

Figure 7:
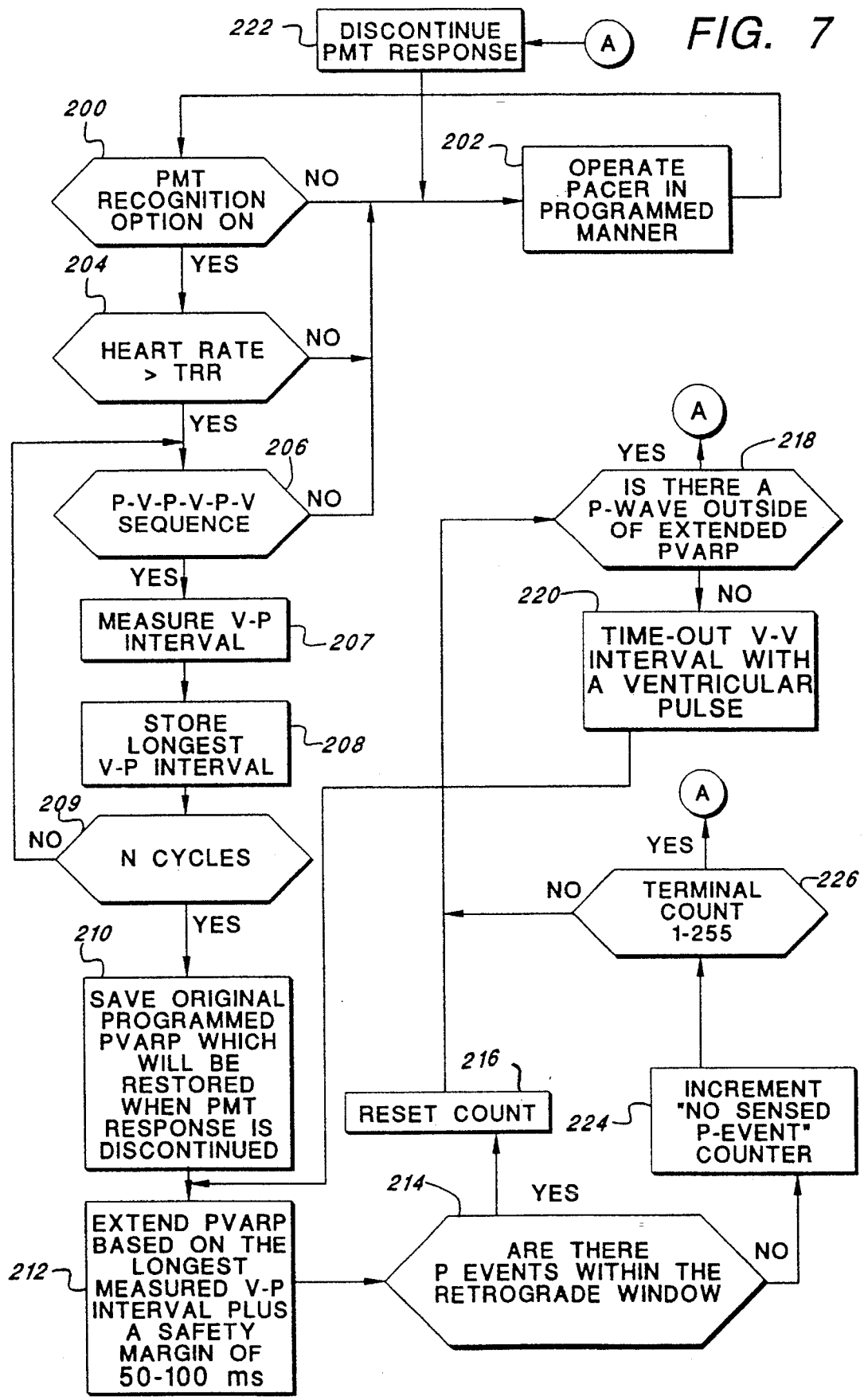
FIG. 7 is a flowchart showing the steps traversed in accordance with another embodiment of the invention to invoke a PMT response, once a PMT is detected, and in order to discontinue such response when no longer needed.

That which has been described thus far relates to the PMT-detection portion of the invention, and is essentially the same PMT-detection scheme described in U.S. Pat. No. 5,074,308. Once a PMT has been detected using this technique, then the present invention advantageously applies a PMT suppression response. Two such PMT suppression responses are contemplated, as illustrated in the flowcharts of FIGS. 5 and 7.

Figure 5:
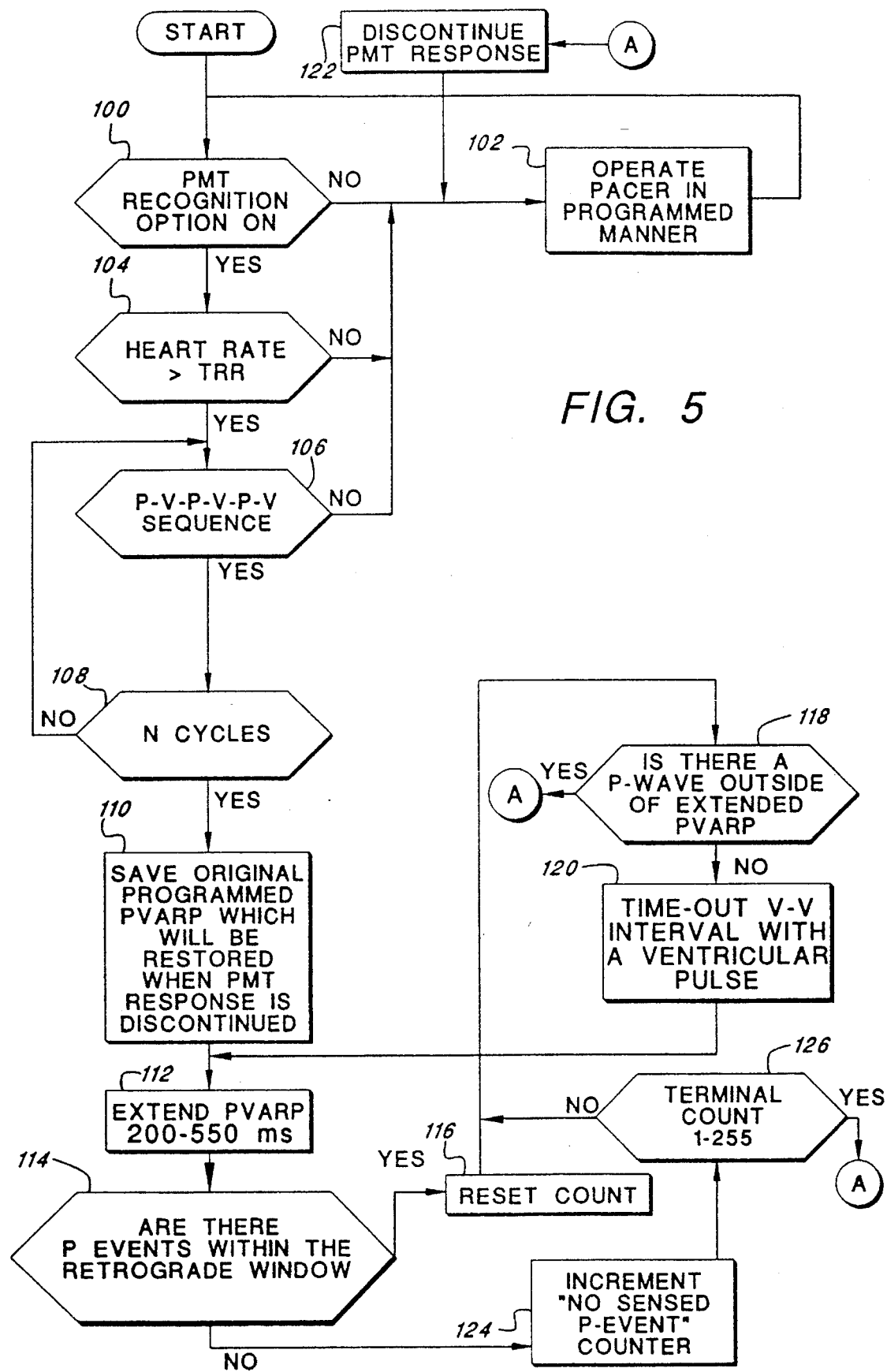
FIG. 5 is a flowchart showing the steps traversed in accordance with one embodiment of the invention to invoke a PMT response, once a PMT is detected, and in order to discontinue such response when no longer needed.

Referring first to FIG. 5, it is seen that the PMT suppression routine first checks (Block 100) whether the PMT recognition features of the invention has been enabled, e.g., by a physician through the telemetry and communications circuit 28 of the pacemaker. If the PMT recognition feature has not been enabled, the cardiac pacer will operate (Block 102) in a programmed manner, as is known in the art, but will continue to check (Block 100) whether the PMT recognition feature has been enabled. If the PMT recognition feature is enabled, and if the heart rate, e.g., the frequency of detected P-waves, is greater than the tachycardia reference rate (TRR) (Block 104), then the PMT suppression routine determines (Block 106) whether a P-V-P-V-P-V . . . sequence, i.e., P-wave, V-pulse, P-wave, V-pulse, P-wave, V-pulse, . . . is present.

If the heart rate is less than the TRR or the P-V-P-V-P-V . . . sequence is not detected, then the cardiac pacer operates in the programmed manner (Block 102). If the P-V-P-V-P-V . . . sequence is detected, then the number of cardiac cycles that has occurred in such sequence is monitored and checked (Block 108) to determine whether a prescribed number of such cycles has occurred. The prescribed number of cycles is programmed by the physician using the telemetry communications circuit 28, as is known in the art. If the prescribed number of cycles has not yet occurred, then the PMT suppression routine continues to check (Block 106) for the P-V-P-V-P-V sequence, as described above. If the prescribed number of cycles has occurred, then the present or existing PVARP interval is saved (Block 110) so that it can be restored when the PMT suppression response is discontinued. The PVARP is then extended (Block 112) by an amount of from 200 to 550 ms, with the physician selecting the exact amount of extension as a function of the particular patient. For example, the physician may choose to extend the PVARP by 300 ms.

Figure 10:
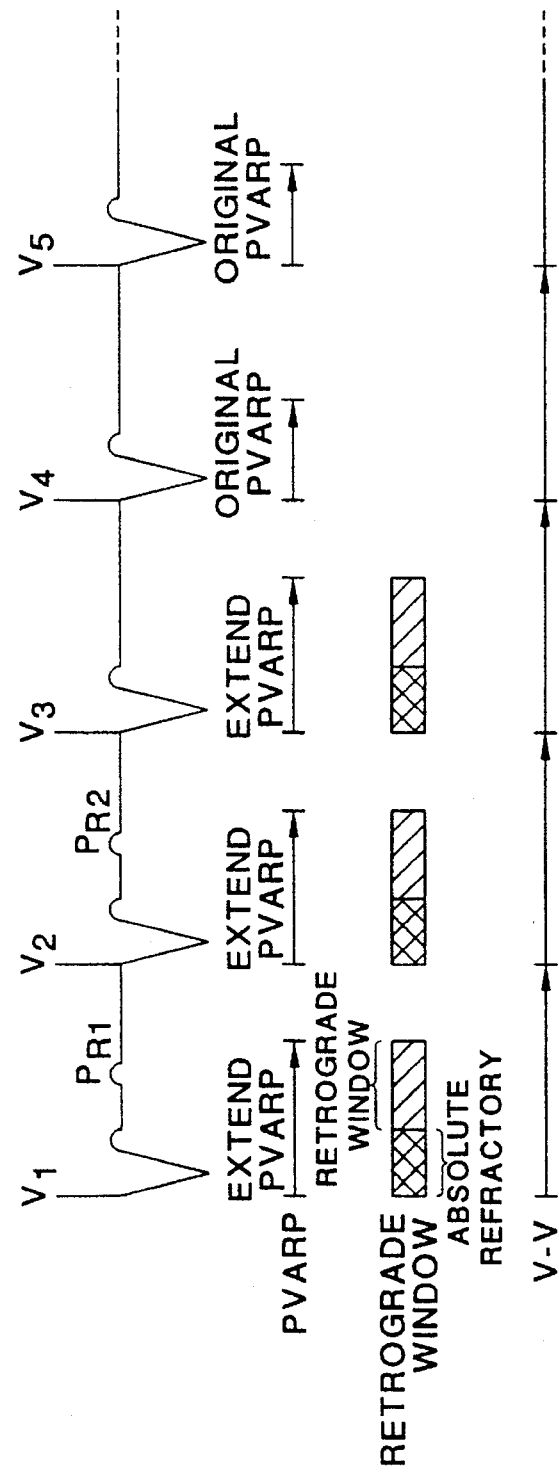
FIG. 10 is a composite timing diagram showing another way in which the invention detects that the PMT response is no longer needed.

After extending PVARP, the PMT suppression routine next determines (Block 114) whether P-wave events have been detected within a retrograde window. The retrograde window is shown in FIG. 10 and consists of that portion of the extended PVARP beyond an absolute refractory portion of the extended PVARP. The absolute refractory portion of PVARP is commonly used in all pacemakers to mask the pacer pulse artifact from the sense amplifiers. The absolute refractory portion of PVARP is usually set to be 50 to 150 msec. Hence, if the extended PVARP is set to be approximately 350 ms, and if the absolute refractory portion of PVARP is 100 ms, then the retrograde window is 250 ms.

In accordance with the present invention, P-wave events that occur within the retrograde window are deemed to be retrograde P-waves, and the occurrence of such retrograde P-waves, if any, are monitored (Block 114). When a retrograde P-wave occurs within the retrograde window, a counter is reset (Block 116). Such counter, as explained below, counts the number of retrograde windows (i.e., cardiac cycles) that go by without a retrograde P-wave appearing therein. The counter is thus incremented for each cardiac cycle wherein a retrograde P-wave does not occur (and may thus be viewed as a "No Sensed P-Event" counter). When a P-event does occur within the retrograde window (YES branch of Block 114), and the counter is reset (Block 116), a determination is then made (Block 118) as to whether a P-wave occurs outside of the extended PVARP. If no P-wave occurs outside the extended PVARP, then the V-V interval is timed-out (Block 120) upon which a ventricular pulse is generated, and the PVARP remains extended (Block 112), with processing continuing as described above. If a P-wave occurs outside the extended PVARP, such P-wave is deemed a sinus P-wave, and its occurrence triggers the discontinuance of the PMT suppression response (Block 122). Such termination of the PMT response is triggered, for example, by P-wave $P_1$ in FIG. 9, which means that the original PVARP is restored and the pacer operates in the programmed manner (Block 102), with processing continuing with the determination (Block 100) of whether PMT recognition is on, as described above.

If no P-wave events occur within the retrograde window, then the "No Sensed P-Event" (NSPE) counter, mentioned above, is incremented (Block 124). The NSPE counter is then checked (Block 126) to see whether it has reached its programmed terminal count. The terminal count, n, may be, e.g., from 1 to 255, and is programmed by the physician using the telemetry/communications circuit 28, described above. If the terminal count of the NSPE counter has not been reached (NO branch of Block 126), processing continues with the determination (Block 118) of whether any P-wave occurs outside the extended PVARP, as described above. If the terminal count of the NSPE counter has been reached (YES branch of Block 126), then that indicates that n cardiac cycles have elapsed without the occurrence of a retrograde P-wave, and hence that the PMT suppression response is probably no longer needed. As a result, the PMT suppression response is discontinued (Block 122), and processing continues as described above. In this way, a pacer mediated tachycardia (PMT) is first detected and then responded to by extending PVARP by a programmed amount. PVARP remains extended until either a sinus P-wave is sensed after the extended PVARP, or until n cardiac cycles occur without the occurrence of a retrograde P-wave, whichever occurs first, at which time PVARP is returned to its initial value.

Figure 6:
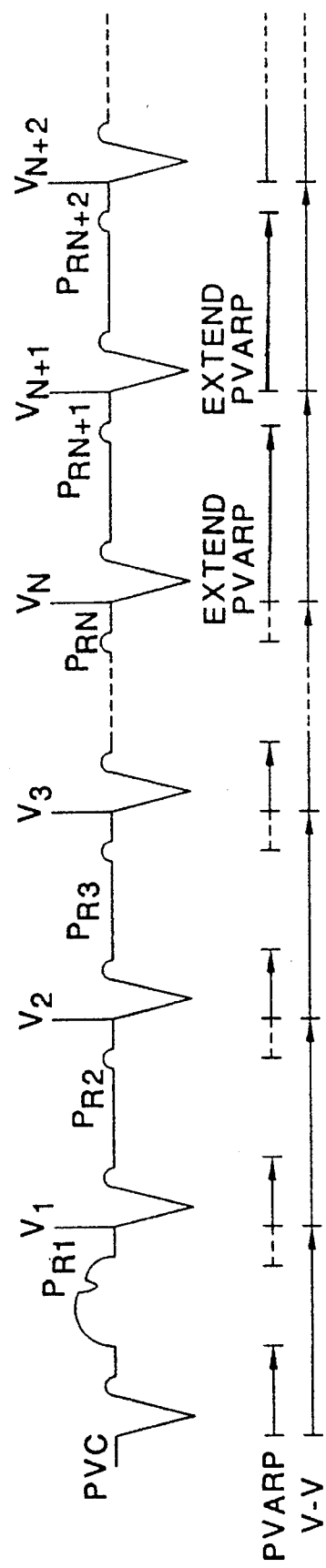
FIG. 6 is a composite timing diagram illustrating the PMT response invoked by the method of FIG. 5.

FIG. 6 shows a composite timing diagram that illustrates the detection and response to a PMT in accordance with the PMT suppression routine of FIG. 5. The onset of the PMT begins with a premature ventricular contraction (PVC), which starts retrograde conduction, resulting in the retrograde P-wave $P_{R1}$. The retrograde P-wave $P_{R1}$ occurs after the PVARP, so it is detected, causing a V-pulse $V_1$ to occur one P-V delay thereafter. This process continues until a programmed number of retrograde P-waves $P_{R1}$, $P_{R2}$, $PR_3$ ... $P_{RN}$ have occurred, each being followed by a corresponding V-pulse. Three such V-pulses, $V_1$, $V_2$, $V_3$ are shown in FIG. 6, followed by a final detected retrograde-induced V-pulse, $V_N$. A cycle counter keeps track of the number of cardiac cycles of such P-V-P-V ... sequence that must occur before triggering the PMT suppression response of the invention. The number of cycles N necessary to trigger the PMT suppression response may be programmed by the physician using the telemetry/communications circuit 28, and may range from, e.g., 3 to 10. After the programmed number N of cardiac cycles has been counted, the PVARP is extended beginning with the last counted V-pulse, $V_N$. The extended PVARP continues to be utilized during subsequent V-pulses $V_{N+1}$, $V_{N+2}$, etc., and continues to be used until the PMT suppression response of FIG. 5 is terminated, as illustrated more fully below in FIGS. 9 and 10.

Referring next to FIG. 7, a flowchart is shown of an alternate PMT suppression routine, similar to the PMT suppression routine of FIG. 5. The only difference between the method of FIG. 5 and the method of FIG. 7 is that the amount of the PVARP extension in FIG. 7 is not a programmed amount as it is in FIG. 5, but is rather a calculated amount based on a prior measurement of the V-P interval and a programmed safety factor. More particularly, as seen in FIG. 7, and as explained more fully below, as the PMT recognition steps are carried out (i.e., as a determination is made as to whether a P-V-P-V-P-V ... sequence is occurring at a rate above TRR), the V-P interval is measured, with the longest V-P interval being stored in memory. This stored V-P interval is then used to define the length of the extended PVARP, with the extended PVARP being set to a value equal to the longest V-P interval plus a safety margin.

Turning to FIG. 7, it is seen that the PMT suppression routine first checks (Block 200) whether PMT recognition has been enabled. If the PMT recognition feature has not been enabled, the cardiac pacer will operate (Block 202) in the programmed manner, as is known in the art, but continues to check (Block 200) whether the PMT recognition feature has been enabled. If PMT recognition is enabled, and the heart rate, e.g., the frequency of detected P-waves, is greater than the tachycardia reference rate (TRR) (Block 204), then the PMT suppression routine determines (Block 206) whether a P-V-P-V-P-V ... sequence is present.

If the heart rate is less than the TRR, or the P-V-P-V-P-V ... sequence is not detected, then the cardiac pacer operates in the programmed manner (Block 202). In the event the P-V-P-V-P-V ... sequence is detected, then the V-P interval of each cycle of such sequence is measured (Block 207), and compared with a previously stored V-P interval. If the measured V-P interval is longer than the stored V-P interval, then the new measured V-P interval is stored (Block 208), replacing the previously stored V-P interval. In this manner, the longest V-P interval is thus always stored. Next, a cardiac cycle counter is incremented and checked (Block 209) to determine whether a prescribed number N of cardiac cycles has been detected. If not, the process repeats. As the process repeats, the longest V-P interval of the sequence will always be the V-P interval that is stored.

Once the prescribed number of cycles has been detected ("Yes" branch of Block 209), then the value of the original programmed PVARP interval is saved (Block 210) so that it can be restored when the PMT suppression response is discontinued.

After the original programmed PVARP is stored, PVARP is extended (Block 212) by an amount based on the stored longest measured V-P interval (from Block 208) plus a safety margin of from 50 to 100 ms, e.g., 75 ms.

The PMT suppression routine then determines (Block 214) whether P-wave events have been detected within the retrograde window. The retrograde window is shown in FIG. 10 and consists of that portion of the extended PVARP in excess of an absolute refractory portion of the extended PVARP.

If there are P-wave events within the retrograde window, the NSPE counter is reset (Block 216), and a determination is made (Block 218) as to whether there is a P-wave outside of the extended PVARP (which would be a sinus P-wave). If no P-wave occurs outside the extended PVARP, then the V-V interval is timed-out (Block 220), a ventricular pulse is generated, and the PVARP remains extended (Block 212), with processing continuing as described above. If a P-wave occurs outside the extended PVARP, e.g., P-wave $P_1$ in FIG. 9, then such P-wave is deemed a sinus P-wave, and its occurrence causes the PMT suppression response to be discontinued (Block 222), i.e., the original PVARP is restored and the pacer operates in the programmed manner (Block 202), as described above.

If no retrograde P-wave events occur within the retrograde window, e.g., as occurs after V-pulse $V_3$ in FIG. 10, then the NSPE counter is incremented (Block 224) and checked (Block 226) to see whether its count has reached the terminal count, n, described above. If the terminal count has not been reached, processing continues with the determination (Block 218) of whether a P-wave has occurred outside the extended PVARP. If the terminal count has been reached, then the PMT suppression response is discontinued (Block 222), with processing continuing as described above. In this way, a pacer mediated tachycardia (PMT) is first detected and then responded to by extending PVARP by a calculated amount. The PVARP remains extended until either a sinus P-wave is sensed after the extended PVARP, or until n cardiac cycles occur without the occurrence of a retrograde P-wave, whichever occurs first, at which time PVARP is returned to its initial value. Advantageously, the amount by which PVARP is extended is based on a measured V-P interval so that PVARP is not extended too much, but is rather only extended as much as is necessary to block the retrograde P-waves. This affords sinus P-waves a better chance of being detected and tracked, so that the proper A-V synchrony of the heart may be maintained.

Figure 8:
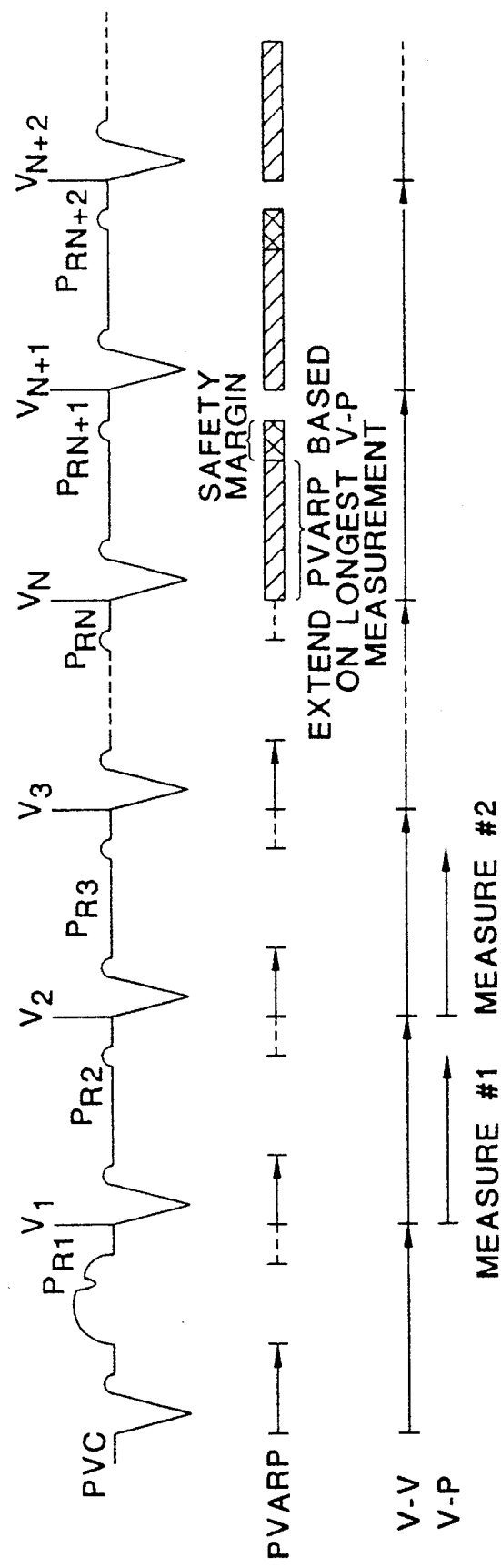
FIG. 8 is a composite timing diagram illustrating the PMT response invoked by the method of FIG. 7.

Referring next to FIG. 8, a composite timing diagram is illustrated that depicts the detection and response to a PMT using the method shown in FIG. 7. The PMT begins with a PVC, which starts retrograde conduction as shown by retrograde P-wave $P_{R1}$. A first V-pulse $V_1$ is generated by the cardiac pacer one P-V delay after sensing the first retrograde P-wave $P_{R1}$. After the first retrograde P-wave $P_{R1}$ is detected and the first V-pulse $V_1$ is generated, the next V-P interval is measured (measure #1) and stored. The next retrograde P-wave $P_{R2}$ is then detected and in response thereto a second V-pulse $V_2$ is generated, with the V-P interval being measured (measure #2), and stored if it is larger than the previously stored V-P interval. After the V-P interval has been measured, and possibly stored, and the P-V-P-V-P-V . . . sequence has continued for a prescribed number of cycles, the PVARP is extended so that it equals the longest stored V-P interval measurement plus a safety margin. This occurs after the V-pulse $V_N$ corresponding to the prescribed number of cycles. The safety margin, which is from between 50 and 100 ms, e.g., 75 ms, is thus added to the stored longest V-P interval to determine the length of the extended PVARP.

Figure 9:
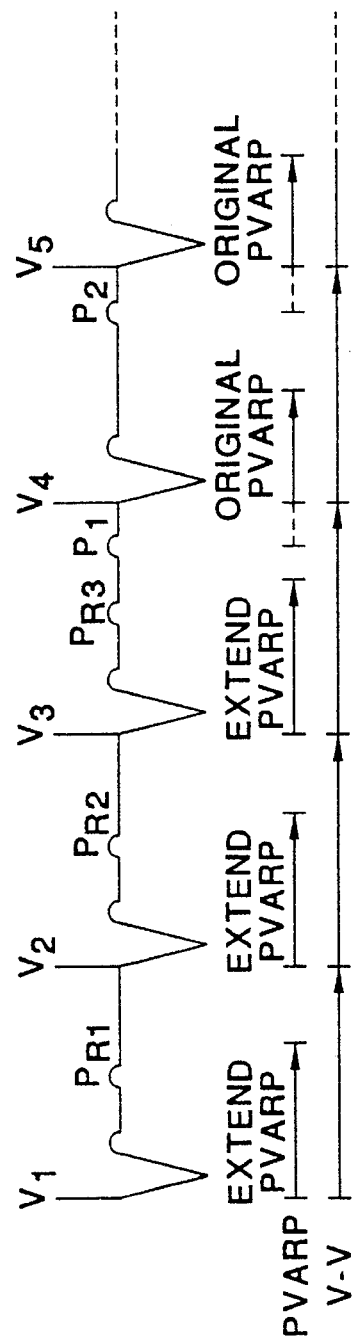
FIG. 9 is a composite timing diagram showing one way in which the invention detects that the PMT response is no longer needed.

Referring next to FIGS. 9 and 10, composite timing diagrams are shown illustrating the two methods used by the invention to discontinue the PMT suppression response (i.e, to discontinue the extended PVARP). Extending PVARP for prolonged periods of time is not viewed as a desirable condition because sinus P-waves are likely to also be blocked, and hence not tracked, by the extended PVARP, particularly, as the P-wave rate changes (increases). Hence, the present invention returns PVARP to its initial value just as soon as it detects that the retrograde P-waves have stopped. If a P-wave is sensed outside of the extended PVARP, for example, then this P-wave is deemed to be a sinus P-wave. As such, it is tracked with a subsequent V-pulse after a PV delay, as shown in FIG. 9. As seen in FIG. 9, first, second and third retrograde P-waves, $P_{R1}$, $P_{R2}$ and $P_{R3}$ are shown as occurring during respective extended PVARP periods. Following the third retrograde P-wave $P_{R3}$, a non-retrograde P-wave $P_1$, occurs outside the extended PVARP. The occurrence of the non-retrograde P-wave $P_1$ signals the end of the PMT. In response to the non-retrograde P-wave $P_1$, the PMT response is thus discontinued by restoring the original PVARP, as described in FIGS. 5 and 7. In this way, the PMT response is terminated through detection of a non-retrograde (sinus) P-wave $P_1$, which signals the end of the PMT.

Referring next to FIG. 10, another way of discontinuing the PMT suppression response is illustrated. That which is shown in FIG. 10 is basically a technique for looking for missing retrograde P-waves within the retrograde window, and if a sufficient number of such missing retrograde P-waves are detected, then that is used as an indication that the retrograde P-waves have stopped. As seen in FIG. 10, the extended PVARP is divided into two subperiods. The first subperiod is an absolute refractory period during which no atrial events are detected due to a high degree of noise in the sensed signal following the V-pulse. Following the absolute refractory period, but before the end of the extended PVARP, a retrograde window is defined during which P-waves are detected, but not used to initiate the P-V interval. Any P-wave that is detected within the retrograde window is deemed to be a retrograde P-wave.

As shown in the example of FIG. 10, first and second V-pulses $V_1$, $V_2$ are generated by the cardiac pacer following corresponding first and second retrograde P-waves $P_{R1}$, $P_{R2}$. These retrograde P-waves $P_{R1}$, $P_{R2}$ occur during respective retrograde windows. Following a third V-pulse $V_3$, no retrograde P-wave is detected during the corresponding retrograde window. The nonoccurrence of the retrograde P-wave causes the NSPE counter, described above, to be incremented. When the NSPE counter reaches a terminal count (which is 1 for the case shown in FIG. 10, but which could be any desired number, e.g., 1 to 255) the original PVARP is restored beginning with a fourth V-pulse $V_4$ (and for subsequent V-pulses following thereafter) until a new PMT is again detected by the pacer's sensing circuits. In this additional way, a PMT condition is first detected, a PMT suppression response is made thereto, and the PMT response is terminated when no further retrograde P-waves are detected.

While the invention herein disclosed has been described by means of specific embodiments and applications thereof, numerous modifications and variations could be made thereto by those skilled in the art without departing from the scope of the invention set forth in the claims.

What is claimed is:

1. In a patient having an implanted pacemaker, a method for detecting and suppressing a pacemaker mediated tachycardia (PMT), the pacemaker including: sensing means for sensing P-waves; pulse generation means for generating a V-pulse; and timing means for defining a PV delay that begins upon sensing a P-wave, after which a V-pulse is generated, whereby sensed P-waves are tracked with a V-pulse that occurs one PV delay thereafter, and a post ventricular atrial refractory period (PVARP) that begins following a V-pulse, and during which P-waves are not tracked, said method comprising the steps of:

detecting a PMT; and suppressing the PMT in response to the detecting of the PMT, by:

increasing the PVARP of the pacemaker from an initial PVARP to an extended PVARP;

sensing if a P-wave occurs following the extended PVARP within at least one of a plurality of subsequent cardiac cycles; and maintaining the PVARP at the extended PVARP in the absence of a P-wave being sensed following the extended PVARP;

restoring the PVARP to its initial PVARP in response to a P-wave being sensed following the extended PVARP within the at least one of the plurality of subsequent cardiac cycles.

2. The method of claim 1, wherein the step of increasing the PVARP comprises:

storing a V-P interval of one of a plurality of previous cardiac cycles;

adding a safety period to the V-P interval previously stored; and defining the extended PVARP to be equal to the stored V-P interval plus the safety period.

3. The method of claim 2, wherein the adding of the safety-period includes adding at least 50 ms to the stored V-P interval.

4. The method of claim 2, wherein the storing of the V-P interval includes:

selecting a longest V-P interval from V-P intervals in at least a portion of the plurality of previous cardiac cycles; and storing the longest selected V-P interval.

5. The method of claim 1, wherein the pacemaker further includes a counter, and wherein the suppression of the PMT further includes:

sensing a P-wave during the extended PVARP within the at least one of the plurality of subsequent cardiac cycles;

resetting a counter in response to the sensing of a P-wave during the extended PVARP within the at least one of the plurality of subsequent cardiac cycles;

incrementing the counter in response to an extended PVARP interval, within the plurality of subsequent cardiac cycles, during which a P-wave is not sensed, whereby the counter counts the absence of P-events during the extended PVARP;

determining whether a count maintained by the counter has reached a terminal count n; and restoring the PVARP to the initial PVARP in response to determining that the count held in the counter has reached the terminal count n, whereby the PVARP is restored to its initial value whenever n cardiac cycles occur without a P-wave having been sensed during the extended PVARP.

6. The method of claim 5, wherein sensing a P-wave during the extended PVARP includes sensing a P-wave within a retrograde window portion of the extended PVARP, the retrograde window portion comprising a latter portion of the extended PVARP following an absolute refractory portion.

7. The method of claim 6, wherein detecting the PMT includes:

sensing a P-wave followed by a V-pulse within each of a plurality of previous cardiac cycles;

sensing if the plurality of previous cardiac cycles occurs at a rate in excess of a tachycardia reference rate (TRR);

measuring a V-P interval of at least one of the plurality of previous cardiac cycles, the V-P interval comprising the time period between a V-pulse and a next succeeding P-wave;

increasing a P-V interval in a single cardiac cycle following the plurality of previous cardiac cycles in the event the plurality of previous cardiac cycles occurs at a rate in excess of the TRR, the P-V interval comprising a time interval between a P-wave and a V-pulse within the single cardiac cycle;

measuring the V-P interval of the single cardiac cycle, the V-P interval comprising a time interval between a V-pulse and a P-wave within the single cardiac cycle;

sensing whether the V-P interval of the single cardiac cycle remains substantially unchanged from the V-P interval of the at least one of the plurality of previous cardiac cycles; and concluding that a PMT is present when the V-P interval of the single cardiac cycle remains substantially unchanged.

8. In a patient having an implanted dual chamber pacemaker, a method for detecting and suppressing a pacemaker mediated tachycardia (PMT), the pacemaker including: sensing means for sensing P-waves; pulse generation means for generating a V-pulse; and timing means for defining a PV delay that begins upon sensing a P-wave, after which a V-pulse is generated, whereby sensed P-waves are tracked by generating a V-pulse one PV delay thereafter, and a post ventricular atrial refractory period (PVARP) that begins following a V-pulse, and during which P-waves are not tracked, said method comprising the steps of:

determining if a PMT is present; and suppressing the PMT by:

extending the PVARP of the pacemaker from an initial value to an extended value, whereby an extended PVARP is generated;

sensing the occurrence of a P-wave; maintaining the PVARP at the extended PVARP in the absence of a P-wave being sensed following the extended PVARP;

restoring the PVARP to its initial value if: (1) a P-wave is sensed following the extended PVARP within at least one of the plurality of subsequent cardiac cycles, or (2) a prescribed number of subsequent cardiac cycles elapse without a P-wave being sensed during the extended PVARP, whichever occurs first.

9. The method of claim 8, wherein the step of determining if a PMT is present comprises:

monitoring the P-waves and V-pulses of a recurring P-wave, V-pulse, P-wave, V-pulse, . . . sequence;

detecting whether a V-P time interval of such sequence remains stable in the face of a changing PV delay;

detecting whether the V-pulses are generated at a rate that exceeds a tachycardia reference rate (TRR); and if the V-P time interval remains stable, and if the V-pulses occur at rate that exceeds the TRR, then concluding that a PMT is present.

10. The method of claim 8, wherein the step of extending the PVARP includes dividing PVARP into two portions, a first portion of which comprises an absolute refractory portion during which P-waves are not sensed, and a second portion of which comprises a retrograde window during which P-waves may be sensed but not tracked, and further during which any P-wave that is sensed is deemed to be a retrograde P-wave.

11. The method of claim 10, wherein dividing the PVARP into an absolute refractory portion and a retrograde window comprises allocating at least the first 50 ms of the extended PVARP as the absolute refractory portion and at least the last 150 ms of the extended PVARP as the retrograde window.

12. The method of claim 11, wherein the step of restoring the PVARP to its initial value whenever a prescribed number of subsequent cardiac cycles elapse without a P-wave being sensed during the extended PVARP comprises restoring the PVARP to its initial value whenever retrograde P-waves fail to occur during the retrograde window of the extended PVARP for a prescribed number of cardiac cycles n.

13. The method of claim 12, further including defining n, the number of cardiac cycles that must occur without a retrograde P-wave having been sensed before the extended PVARP is returned to its initial value, to be equal to at least one and no more than 255.

14. In a pacemaker having sensing and timing circuits, a method for detecting and suppressing a pacemaker mediated tachycardia (PMT), said method comprising the steps of:

detecting a PMT using the sensing and timing circuits of the pacemaker; and suppressing the PMT once detected by:

increasing a post ventricular atrial refractory period (PVARP) of the pacemaker from an initial value to an extended PVARP;

sensing a P-wave during the extended PVARP within at least one of a plurality of subsequent cardiac cycles;

resetting a no-sensed-P-event (NSPE) count in response to the sensing of a P-wave during the extended PVARP within the at least one of the plurality of subsequent cardiac cycles;

incrementing the NSPE count in response to an extended PVARP interval, within the plurality of subsequent cardiac cycles, during which a P-wave is not sensed;

determining whether the NSPE count reaches a predefined terminal count;

restoring the PVARP to its initial value in response to determining that the NSPE count has reached the terminal count.

15. The method of claim 14, wherein the step of increasing the PVARP comprises:

storing a V-P interval of one of a plurality of previous cardiac cycles;

adding a safety period to the V-P interval having been stored; and generating the extended PVARP by adding the safety period to the V-P interval having been stored.

16. The method of claim 15, wherein storing the V-P interval includes:

selecting a longest V-P interval from a plurality of V-P intervals associated with at least a portion of the plurality of previous cardiac cycles; and storing the longest V-P interval having been selected.

17. The method of claim 16, wherein the step of increasing the PVARP comprises increasing the PVARP by a programmed amount of from 200 to 550 ms.

18. The method of claim 14, wherein the suppression of the PMT further includes:

sensing a P-wave following the extended PVARP within at least one of the plurality of subsequent cardiac cycles; and restoring the PVARP to its initial value in response to the sensing of a P-wave following the extended PVARP within the at least one of the plurality of subsequent cardiac cycles.

19. An implantable dual-chamber pacemaker for detecting and suppressing a pacemaker mediated tachycardia (PMT) comprising:

detecting means for detecting a PMT; and suppressing means for suppressing the PMT once detected, the suppressing means including:

PVARP extension means responsive to the PMT detecting means for extending a post ventricular atrial refractory period (PVARP) of the pacemaker from an initial value to an extended value, thereby creating an extended PVARP;

first sensing means for sensing a P-wave following the extended PVARP within at least one of a plurality of subsequent cardiac cycles; and maintaining means for maintaining the PVARP at the extended PVARP in the absence of a P-wave being sensed following the extended PVARP;

restoring means for restoring the PVARP to its initial value in response to a P-wave being sensed by the first sensing means;

whereby a PMT is detected, suppressed and the PVARP is restored to its initial value.

20. The pacemaker of claim 19, wherein the PVARP extension means comprises:

means for detecting a V-P interval;

memory means for storing the V-P interval of one of a plurality of previous cardiac cycles, the memory means being coupled to the first sensing means;

adding means for adding a safety period to the V-P interval stored by the memory means; and timing means responsive to the adding means for generating the extended PVARP to be equal to the safety period added to the stored V-P interval.

21. The pacemaker of claim 19, wherein the suppressing means further includes:

second sensing means for sensing a P-wave during the extended PVARP within the at least one of the plurality of subsequent cardiac cycles;

an incrementable coupled to the second sensing means, the counter being incremented in response to an extended PVARP interval, within the plurality of subsequent cardiac cycles, during which a P-wave is not sensed by the second sensing means;

reset means for resetting the counter in response to sensing a P-wave with the second sensing means; and processing means coupled to the counter for determining whether the counter reaches a terminal count; and the restoring means being coupled to the processing means and restoring the PVARP to its initial value whenever the counter reaches the terminal count.

22. The pacemaker of claim 19, wherein the PVARP extension means comprises means for dividing the PVARP into an absolute refractory portion followed by a retrograde time window, and wherein said second sensing means only senses P-waves that occur during the retrograde time window, the P-waves thus sensed by the second sensing means being considered as retrograde P-waves.

23. An implantable pacemaker for detecting and suppressing a pacemaker mediated tachycardia (PMT), said pacemaker comprising:

detecting means for detecting a PMT; and

PMT suppressing means responsive to the detecting means for suppressing the PMT, the PMT suppressing means including:

extension means for increasing a PVARP of the pacemaker from an initial value to an extended value, thereby creating an extended PVARP;

sensing means for sensing a P-wave during the extended PVARP within at least one of a plurality of subsequent cardiac cycles;

an incrementable counter coupled to the sensing means, the counter being incremented in response to an extended PVARP interval, within the plurality of subsequent cardiac cycles, during which a P-wave is not sensed by the sensing means;

reset means coupled to the counter for resetting the counter in response to the sensing of a P-wave during the extended PVARP within the at least one of the plurality of subsequent cardiac cycles;

processing means coupled to the counter and reset means for determining whether the counter reaches a terminal count;

restoring means for restoring the PVARP to its initial value in response to the processor means determining that the counter has reached a terminal count.

24. The pacemaker of claim 23, wherein the PMT suppressing means further includes:

second sensing means for sensing a P-wave following the extended PVARP within at least one of the plurality of subsequent cardiac cycles;

said restoring means restoring the PVARP in response to a P-wave being sensed by the second sensing means.

* * * * *